(12) United States Patent
Shanks et al.

(10) Patent No.: US 7,993,382 B2
(45) Date of Patent: Aug. 9, 2011

(54) FAT REDUCTION USING EXTERNAL LASER RADIATION AND NIACIN

(75) Inventors: Steven C Shanks, Mesa, AZ (US); Ryan Maloney, Phoenix, AZ (US)

(73) Assignee: Erchonia Corporation, McKinney, TX (US)

( * ) Notice: Subject to any disclaimer, the term of this patent is extended or adjusted under 35 U.S.C. 154(b) by 994 days.

(21) Appl. No.: 11/522,136

(22) Filed: Sep. 14, 2006
(Under 37 CFR 1.47)

(65) Prior Publication Data
US 2007/0100402 A1 May 3, 2007

Related U.S. Application Data

(63) Continuation-in-part of application No. 11/053,369, filed on Feb. 7, 2005.

(60) Provisional application No. 60/542,720, filed on Feb. 6, 2004.

(51) Int. Cl.
*A61N 5/067* (2006.01)
(52) U.S. Cl. .............................. 607/89; 607/88
(58) Field of Classification Search ............... 607/88–91, 607/100; 606/4–5
See application file for complete search history.

(56) References Cited

U.S. PATENT DOCUMENTS

| 5,143,063 | A | 9/1992 | Fellner |
|---|---|---|---|
| 5,507,790 | A | 4/1996 | Weiss |
| 5,725,482 | A | 3/1998 | Bishop |
| 6,013,096 | A | 1/2000 | Tucek |
| 6,235,016 | B1 | 5/2001 | Stewart |
| 6,328,733 | B1 | 12/2001 | Trost |
| 6,475,211 | B2 | 11/2002 | Chess et al. |
| 6,517,532 | B1 | 2/2003 | Altshuler et al. |
| 6,605,079 | B2 | 8/2003 | Shanks |
| 6,645,162 | B2 | 11/2003 | Friedman et al. |
| 6,673,096 | B2 | 1/2004 | Lach |
| 6,746,473 | B2 | 6/2004 | Shanks et al. |
| 2002/0123743 | A1* | 9/2002 | Shanks et al. ............... 606/2 |
| 2002/0193831 | A1* | 12/2002 | Smith, III ................. 607/2 |
| 2003/0069618 | A1* | 4/2003 | Smith et al. ............... 607/100 |
| 2004/0147984 | A1 | 7/2004 | Altshuler et al. |
| 2004/0181210 | A1* | 9/2004 | Shellman ................. 606/8 |
| 2004/0191278 | A1* | 9/2004 | Christensen .............. 424/401 |
| 2004/0210214 | A1 | 10/2004 | Knowlton |
| 2004/0236252 | A1 | 11/2004 | Muzzi et al. |
| 2005/0197681 | A1 | 9/2005 | Barolet |

FOREIGN PATENT DOCUMENTS

| DE | 197 25 877 A1 | 12/1998 |
|---|---|---|
| DE | 199 45 087 A1 | 3/2001 |
| WO | WO 92/03187 A | 3/1992 |
| WO | WO 93/21993 A | 11/1993 |
| WO | WO 97/16126 A | 5/1997 |

* cited by examiner

*Primary Examiner* — Roy D Gibson
(74) *Attorney, Agent, or Firm* — Etherton Law Group, LLC; Sandra L. Etherton; Ann Marie W. Whitley

(57) ABSTRACT

The present invention is a non-invasive method for reducing fat in a patient by administering a therapeutically effective amount of niacin and applying laser energy to targeted external regions of a patient's body.

1 Claim, 2 Drawing Sheets

FAT REDUCTION USING EXTERNAL LASER RADIATION AND NIACIN

CROSS-REFERENCE TO RELATED APPLICATIONS

This application is a continuation-in-part of co-pending U.S. patent application Ser. No. 11/053,369 filed Feb. 7, 2005 which claims the benefit of U.S. Provisional Application No. 60/542,720 filed Feb. 6, 2004.

FIELD OF INVENTION

This invention relates to a method for non-invasive, non-traumatic shaping and contouring of a human body by external means. In particular, this invention relates to administering niacin to a patient to enhance the effects of applying laser energy to targeted external regions of a patient's body to reduce fat by facilitating the removal of the intracellular fat from fat cells in the targeted areas.

BACKGROUND

There is a great demand to be slimmer and have smoother contours. Many people resort to the cosmetic surgical procedure known as liposuction, wherein excess adipose tissue, also known as fat, is suctioned from the body of a patient. The typical purpose of the liposuction procedure is to leave the patient thinner, with aesthetically more appealing body contours. For example, liposuction is often performed on patients to remove excess fat in the abdominal, buttock, thigh, breast and arm regions of the body.

Adipose tissue is made of adipocytes, or fat cells, which are enclosed membranes filled with globules of triglycerides. In normal fat the fat cells have regular contours and form into grapelike clusters. The intracellular fat is relatively fluid and, if the membrane is pierced, will flow out of the cell into the interstitial space. The interstitial space includes nerves, blood vessels, lymphatics and collagen fibers, among other substances.

Liposuction is performed by inserting a narrow tube, or cannula, through a tiny incision in the skin into the subcutaneous fatty tissue. The cannula is repeatedly pushed then pulled through the fat layer, separating and puncturing the fat cells and suctioning them out. Suction action through the cannula is provided by a vacuum pump or a large syringe. The procedure carries with it some risks and side effects. Due to the physical damage induced, the procedure can damage nerves, lymphatics and vasculature in the surrounding area, often resulting in significant loss of blood as the blood is vacuumed out with the fat and the formation of seroma due to damaged lymphatic channels. In addition, the post-procedure recovery period is long and often accompanied by a great deal of inflammation, bruising and concomitant pain.

Since the liposuction technique was first developed there have been many improvements to the technique, with the goal of making the surgery less dangerous for the patient, as well as reducing the negative aspects of the post-operative recovery period. For example, in the tumescent technique known in prior art, a saline solution containing very dilute amounts of at least an anesthetic and a vasoconstrictor is injected subcutaneously into the area to be suctioned. The anesthetic reduces operative and post-operative pain and the vasoconstrictor helps reduce blood loss. Cannulas have been improved by enabling the cannula to emit laser light and ultrasound energy directly onto the fat cells. This internal application of energy melts the cell wall, releasing the intracellular fat, thereby making the fatty tissue less viscous and more easily suctioned up through the narrow cannula. These procedures suffer the disadvantage of still having to physically stab the cannula repeatedly in the fat layer as well as essentially melting the adipose tissue, resulting in undesirable levels of bruising, inflammation, pain, blood loss, and seroma formation. Recovery time is significant.

In U.S. Pat. No. 6,605,079, issued to one of the inventors of this method and incorporated herein, a less-destructive method is disclosed that uses low energy laser therapy in conjunction with suction of the fat cells. Low level laser therapy (LLLT) has been used increasingly in the treatment of a broad range of conditions such as treatment and repair of injured muscles and tendons. LLLT has improved wound healing, reduced edema, and relieved pain of various etiologies. LLLT has been used successfully post-operative to liposuction to reduce inflammation and pain. While a significant improvement over prior art, it is still invasive and carries with it the corresponding pain and risks.

Non-invasive methods of fat reduction are preferred over invasive methods to minimize trauma to the patient, reduce the risk of infection, and speed up recovery time, among other reasons. To that end, topical agents have long been known which claim to reduce cellulite or at least the appearance of cellulite. Cellulite is a condition that gives the skin a rippled, dimpled appearance. The effect of these agents on cellulite is somewhat dubious, and these agents are not known to actually reduce fat. Some of the topical agents are used in combination with massage or radiation of the affected areas.

To avoid invasive procedures, electromagnetic energy, such as microwave, ultrasound or radio frequency radiation, has also been used to reduce fat. In U.S. Pat. No. 5,507,790 issued to Weiss, a method is described in which a medicament is applied to a patient's skin where fat removal is desired and focused electromagnetic energy is applied to the same work site to heat the fatty tissue and increase fat lipolysis. In U.S. Pat. No. 5,143,063, Fellner takes this method even farther, applying sufficient electromagnetic radiation to destroy the fat cells. Yet another method is to inject an intumescing solution below the skin and apply electromagnetic energy externally to the body. These procedures are disadvantageous in that they utilize such high energy sources that they excessively heat the surrounding tissue, which can result in damage to the tissue and pain. Again, recovery time is significant.

Other external applications of certain types of destructive energy is known in the art. U.S. Pat. No. 6,645,162 issued to Friedman, et al. discloses the superposition of ultrasound waves from two or more sources to create a wave having high intensity localized at the adipose tissue to be treated. With this method, fat cells are sonically disintegrated, allowing the body to dispose of the fat that has been freed. In addition to destruction of cells, another difficulty with this method is accurately obtaining the desired focal zone under the skin.

It is desirable to remove fat with less damage to the fatty tissue, less blood loss, less post-operative bruising, inflammation, and pain than existing methods. Therefore, an object of this invention is to provide a non-invasive method of reducing fat. Another object of this invention is to provide a non-invasive method of reducing cellulite. Another object is to provide a non-invasive method of reducing fat that does not destroy the fat cells, or damage surrounding tissue or structures. Another object is reduce fat using niacin to enhance the effects of low-level laser therapy. It is another object to eliminate the need for recovery time.

SUMMARY OF THE INVENTION

The present invention is a non-invasive method for reducing fat or cellulite in a patient by administering a therapeutically effective amount of niacin and applying laser energy to targeted external regions of a patient's body. The present method helps create smooth contours.

DETAILED DESCRIPTION OF THE INVENTION

Figure 1:
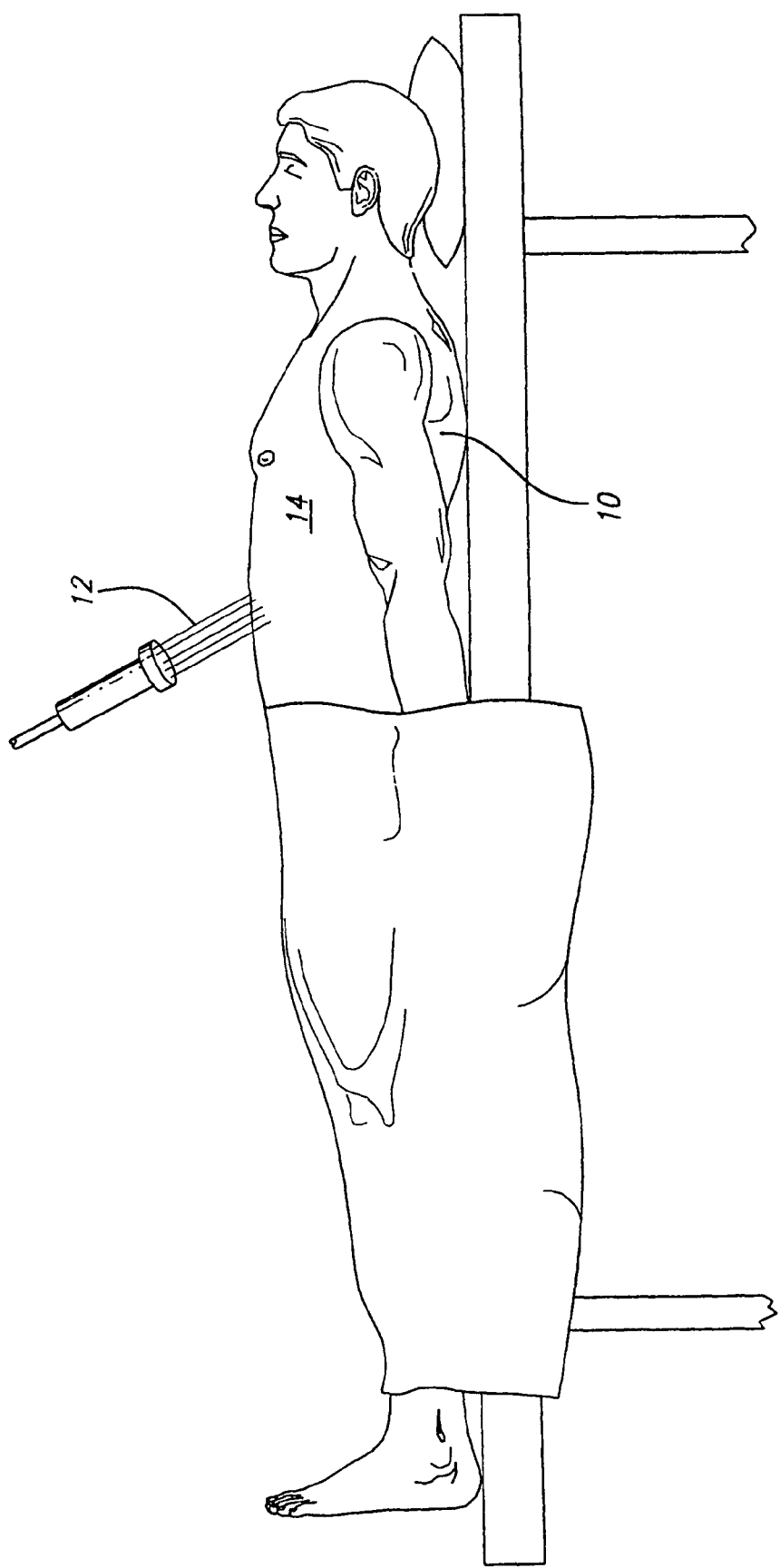
FIG. 1 is a schematic illustration of application of low-level laser radiation.

The present invention combines niacin and low-level laser therapy to reduce fat in a patient and contour the body. Niacin is a water-soluble vitamin necessary for many aspects of health, growth, and reproduction. It is part of the vitamin B complex, and is also known as nicotinic acid or vitamin B-3. Niacin assists in the functioning of the digestive system, skin, and nerves. It is also important for the conversion of food to energy. Niacin is found in dairy products, poultry, fish, lean meats, nuts, and eggs. Legumes and enriched breads and cereals also supply some niacin.

Niacin can be administered orally, topically, sublingually, nasally, intravenously or otherwise parenterally. As used herein, a therapeutic amount of niacin is the amount that increases the amount of fat metabolized by the patient's body. For example, the therapeutically effective amount of niacin administered orally can be about 500 mg or more than about 15 mg. The therapeutically effective amount of niacin administered topically can be about 7 g. In the preferred embodiment, niacin is administered in a therapeutic amount orally, by tablet or liquid. Niacin is administered to the patient over a span of about two weeks. About 500 mg is taken per day during the first day and increased until the patient is taking about 1500 mg per day on the eleventh day. Preferably the patient is given 500 mg the first day in a single dose, and 100 mg is added each day to the dose until the patient is taking 1500 mg per dose. While most patients can tolerate relatively high doses of niacin, for example up to 3 grams a day, even smaller doses than those of the preferred embodiment can be associated with skin flushing and itching. It is desirable to keep the dose low enough to prevent the patient from being uncomfortable. The amount of niacin that is well-tolerated will differ for each patient. Similarly, the effect of the niacin and laser therapy will differ for each patient. The total amount of niacin administered, dose, timing and length of administration will vary for each patient, depending on the patient's tolerance, weight, body fat mass, and lean body mass, among other factors.

In another embodiment, niacin is administered topically to the patient in a therapeutic amount over a span of about two weeks. In a preferred embodiment, 7 grams of niacin is applied daily to the desired area. The niacin is carried in a lotion. For example, a 20% niacin formulation is composed of Nia-112, commonly known as dodecyl nicotinate and nicotinic acid dodecyl ester included in a mixture of conventional ingredients found in a water- or lipid-soluble base. One such lotion comprises a nonionic surfactant such as Brij 58 (polyoxyethylene 20 cetyl ether), cetostearyl alcohol, glyceryl monostearate, polyethylene glycol 400 monostearate, propylene glycol, sorbitol (70%), petrolatum, sorbic acid, simethicone, and butylated hydroxytoluene. As with the oral administration, the amount of niacin that is well-tolerated will differ for each patient. Similarly, the effect of the niacin and laser therapy will differ for each patient. The total amount of niacin administered, dose, timing and length of administration will vary for each patient, depending on the patient's tolerance, weight, body fat mass, and lean body mass, among other factors.

Upon the administration of niacin, laser energy 12 is applied to the adipocyte tissue externally through the skin 14 of the patient, as illustrated in FIG. 1. Sufficient laser energy is applied to release at least a portion of the intracellular fat 23 into the interstitial space 32. The released intracellular fat is removed from the body through the body's normal systems, such as metabolic, lymphatic or excretory systems. The procedure may be repeated in one or more additional areas to remove additional fat there. In that event, additional laser energy would be applied externally to the new area. In this manner, specific areas of the body are contoured.

Typically, fat leakage into the interstitial space is seen as early as 3-5 minutes of laser energy application. This leakage continues for treatments as long as about 12-15 minutes with no fat cell destruction. The preferred treatment is about 30 minutes of laser energy application, three times a week for about two weeks. The laser energy is preferably applied by a scanning laser. Alternatively, the laser energy can be applied by a therapist freely moving a non-scanning laser energy source over the area desired for improved contouring or fat reduction. Alternatively, the laser energy can be emitted from a stationary source, such as an arm that emits laser energy which is attached to a wall or a stand.

Figure 2:
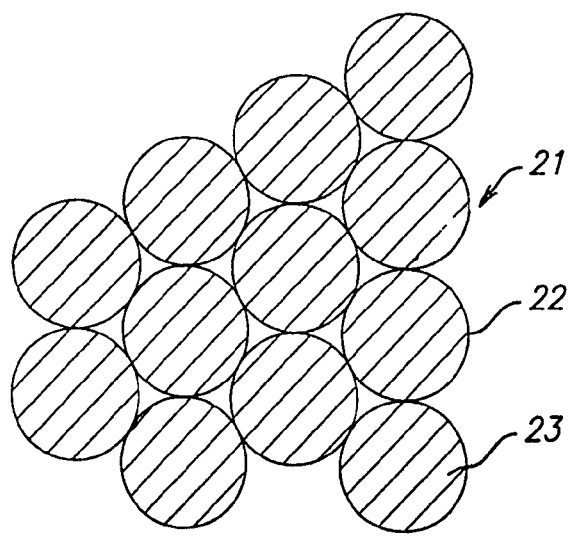
FIG. 2 is a schematic illustration of normal fat cells.
Figure 3:
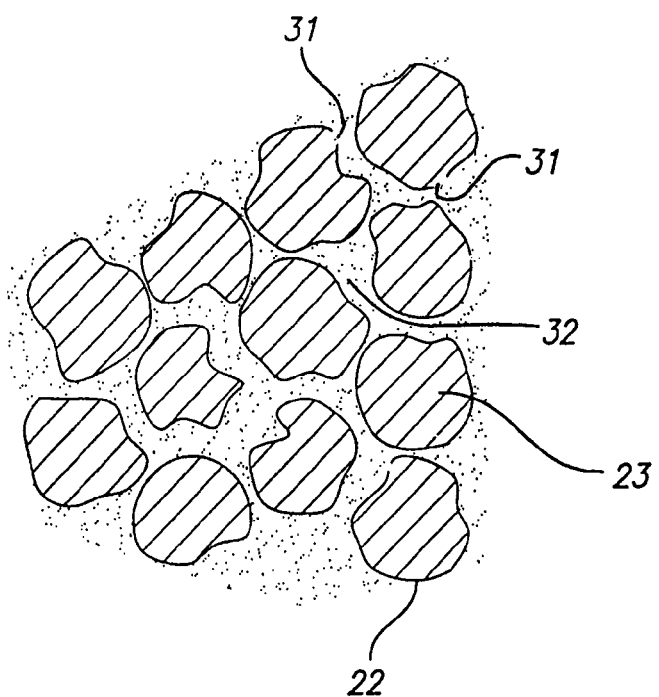
FIG. 3 is schematic illustration of fat cells after externally-applied low-level laser radiation.

The mechanism involved in releasing the intracellular fat from the cells is believed to be the formation of a transitory pore in the cell membrane. FIG. 2 illustrates adipose tissue comprising normal fat cells 21 wherein the cell membrane 22 is filled with intracellular fat 23. Upon sufficient doses of low-level laser energy, the cell membrane 22 is momentarily disrupted, releasing the intracellular fat 23. See FIG. 3, which illustrates pores 31 in the cellular membrane 22 which have released intracellular fat 23 into the interstitial space 32. Upon cessation of the energy application, the pores 31 close and the cell membrane 22 returns to contiguity. The fat cell is not destroyed, provided the duration of laser treatment is appropriate. For a 635 nm laser of less than 1 W, treatments of less than about 12 minutes do not destroy cells.

Once released into the interstitial space, the fat is metabolized by normal processes within the body. The administration of a therapeutic amount of niacin increases the amount of fat that is metabolized. The mechanism is believed to be increased oxidation of the fatty acids and triglycerides by biochemically active forms of niacin such as nicotinamide adenine dinucleotide ($NAD^+$). As known in the art, one of the steps in the breakdown of fatty acids and glycolysis is the use of $NAD^+$ to produce ATP. In addition to niacin's ability to oxidize molecules, niacin is also a vasodilator. With the relaxation and dilation of nearby blood vessels, it is possible for the fatty acids and triglycerides to be absorbed into the blood stream rather than reabsorbed by the adipocyte cell.

The laser energy applied is low level, that is, the treatment has a dose rate that causes no immediate detectable temperature rise of the treated tissue and no macroscopically visible changes in tissue structure. The laser energy penetrates the skin and is specific to the depth of the desired zone of fat to be treated. Consequently, the treated and surrounding tissue is not heated and is not damaged. Preferably the laser light is visible to the human eye so that the area of application is easily determined. A laser device that provides this low-level energy is known in the art as a cold laser, such as the inventions described in U.S. Pat. Nos. 6,013,096 issued to Tucek and 6,746,473, issued to Tucek and Shanks. The preferred laser is a semiconductor diodes emitting laser light at 625 nm.

Other lasers known in the art for use in low-level laser therapy include Helium-Neon lasers having a 632 nm wavelength and semiconductor diode lasers with a broad range of wavelengths between 405-1500 nm. Diode lasers at 633 nm, 670 nm and 1064 nm (infrared) have been shown to work with varying degrees of success. The laser device may have one or more laser energy sources. Different therapy regimens require diodes of different wattages. The preferred laser diodes use less than one watt of power each to simultaneously facilitate liposuction, treat post-operative inflammation, and post-operative pain. Diodes of various other wattages may also be employed to achieve the desired laser energy for the given regimen. Low-level lasers are available commercially.

The dosage of laser energy required to achieve release of the intracellular fat into the interstitial space will vary depending on the thickness of the patient's skin, thickness of fatty tissue, and other biological factors peculiar to each patient. The following preferred embodiment is illustrative.

A patient is administered 500 mg of niacin orally by tablet on a first day. The next day, the patient is administered 600 mg of niacin orally by tablet. The patient is treated with a 635 nm semiconductor diode laser with maximum power of 10 mW to apply laser light to a patient's pads of fat located in the area near his waist, around his side and back, commonly referred to as "love handles." The laser energy is applied for 30 minutes using a scanning laser.

The third day the patient is administered 700 mg of niacin, 800 mg on the fourth day, 900 mg on the fifth day, 1000 mg on the sixth day, all orally by tablet. The patient is again treated for 30 minutes with a 635 nm semiconductor diode laser to the patient's love handles.

The seventh day the patient is administered 1100 mg of niacin, 1200 mg on the eighth day, and 1300 mg on the ninth day. The patient is again treated for 30 minutes with a 635 nm semiconductor diode laser to the patient's love handles.

On the tenth day of niacin administration, the patient is administered 1400 mg of niacin and 1500 mg on the eleventh day through the 14th day. The patient is again treated for 30 minutes with a 635 nm semiconductor diode laser to the patient's love handles. The love handles are reduced, and the patient suffered no pain or bruising.

While there has been illustrated and described what is at present considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed as the best mode contemplated for carrying out the invention, but that the invention will include all embodiments falling within the scope of the appended claims.

We claim:

1. A method for reducing fat in a patient comprising:
    a) administering to the patient a therapeutically effective amount of niacin; and
    b) applying laser energy to the tissue of the patient with no temperature rise of the lasered and surrounding tissue;
    wherein the therapeutically effective amount of niacin is administered orally over a span of at least 11 days and about 500 mg of niacin is administered the first day and the niacin amount is increased until the patient is administered about 1500 mg on the eleventh day.

\* \* \* \* \*